(12) United States Patent
Kim et al.

(10) Patent No.: US 8,962,901 B2
(45) Date of Patent: *Feb. 24, 2015

(54) METHOD OF PRODUCING VALUABLE AROMATICS AND OLEFINS FROM HYDROCARBONACEOUS OILS DERIVED FROM COAL OR WOOD

(75) Inventors: Hong Chan Kim, Jeju-si (KR); Yong Seung Kim, Seoul (KR); Sung Won Kim, Seoul (KR); Sang Hun Oh, Seongnam-si (KR); Hyuck Jae Lee, Daejeon (KR); Dae Hyun Choo, Busan (KR); Cheol Joong Kim, Daejeon (KR); Gyung Rok Kim, Daejeon (KR); Myoung Han Noh, Daejeon (KR); Jae Suk Koh, Daejeon (KR); Hyun Chul Choi, Daejeon (KR); Eun Kyoung Kim, Daejeon (KR); Yoon Kyung Lee, Cheongju-si (KR); Jong Hyung Lee, Gimpo-si (KR); Sun Choi, Daejeon (KR); Seung Hoon Oh, Seoul (KR); Jae Hyun Koh, Daejeon (KR); Sang Il Lee, Daejeon (KR); Seung Woo Lee, Daejeon (KR)

(73) Assignee: SK Innovation CO., Ltd., Seoul (KR)

(*) Notice: Subject to any disclaimer, the term of this patent is extended or adjusted under 35 U.S.C. 154(b) by 212 days.

This patent is subject to a terminal disclaimer.

(21) Appl. No.: 13/823,023
(22) PCT Filed: Sep. 15, 2011
(86) PCT No.: PCT/KR2011/006813
§ 371 (c)(1),
(2), (4) Date: Mar. 25, 2013
(87) PCT Pub. No.: WO2012/036484
PCT Pub. Date: Mar. 22, 2012

(65) Prior Publication Data
US 2013/0178673 A1 Jul. 11, 2013

(30) Foreign Application Priority Data
Sep. 16, 2010 (KR) .......................... 10-2010-0091052

(51) Int. Cl.
C07C 4/06 (2006.01)
C07C 5/02 (2006.01)
(Continued)

(52) U.S. Cl.
CPC ................. $C07C\ 5/13$ (2013.01); $C07C\ 5/2732$ (2013.01); $C07C\ 6/126$ (2013.01); $C07C\ 7/04$ (2013.01);
(Continued)

(58) Field of Classification Search
CPC ............ C10G 1/00; C10G 1/02; C10G 1/006; C10G 1/06; C10G 35/00; C10G 35/04; C10G 45/44; C10G 45/48; C10G 45/50; C10G 55/00; C10G 55/06; C10G 57/005; C10G 69/00; C10G 69/12; C10G 69/123; C10G 2400/20; C10G 2400/30; C07C 5/00; C07C 5/10; C07C 5/11; C07C 5/12; C07C 15/00; C07C 15/02; C07C 15/04; C07C 15/06; C07C 15/08
USPC .................................. 585/253, 240, 242, 251
See application file for complete search history.

(56) References Cited

U.S. PATENT DOCUMENTS

| | | | |
|---|---|---|---|
| 2003/0019792 A1 | 1/2003 | Chen et al. | |
| 2009/0227823 A1 | 9/2009 | Huber et al. | |
| 2010/0160699 A1* | 6/2010 | Frey et al. ..................... | 585/316 |

FOREIGN PATENT DOCUMENTS

| | | |
|---|---|---|
| CN | 1667089 A | 9/2005 |
| CN | 101305078 A | 11/2008 |
| WO | 2007055488 A1 | 5/2007 |

OTHER PUBLICATIONS

CN2011844845.5, Office Action, Apr. 17, 2014 (10 pages).

(Continued)

Primary Examiner — In Suk Bullock
Assistant Examiner — Philip Louie
(74) Attorney, Agent, or Firm — Abelman, Frayne & Schwab

(57) ABSTRACT

This invention relates to a method of producing aromatics and olefins from oils derived from coal or wood, including partially saturating and cracking the oils derived from coal or wood in a hydrogenation and reaction area, separating them depending on the number of carbons, recirculating heavy oils having 11 or more carbons to the hydrogenation and reaction area, feeding oils suitable for producing BTX to an aromatic separation process and a transalkylation process to recover aromatics, and feeding hydrocarbonaceous components having 5 or less carbons to a light separation process, thus obtaining olefins.

16 Claims, 1 Drawing Sheet

(51) Int. Cl.
*C07C 5/13* (2006.01)
*C07C 5/27* (2006.01)
*C07C 6/12* (2006.01)
*C07C 7/04* (2006.01)
*C10G 45/44* (2006.01)
*C10G 45/50* (2006.01)
*C10G 47/16* (2006.01)
*C10G 65/12* (2006.01)

(52) U.S. Cl.
CPC ......... *C07C 2521/04* (2013.01); *C07C 2529/22* (2013.01); *C10G 45/44* (2013.01); *C10G 45/50* (2013.01); *C10G 47/16* (2013.01); *C10G 65/12* (2013.01); *C10G 2300/1096* (2013.01); *C10G 2400/30* (2013.01); *C10G 2400/20* (2013.01)

USPC ............ 585/253; 585/240; 585/242; 585/251

(56) References Cited

OTHER PUBLICATIONS

Torren R. Carlson, et al., "Aromatic Production from Catalytic Fast Pyrolysis of Biomass-Derived Feedstocks," Topics in Catalysis, vol. 52, pp. 241-252 (2009).

N. Martin, et al., "Copyrolysis of wood biomass and synthetic polymers mixtures. Part II: characterization of the liquid phases," Journal of Analytical and Applied Pyrolysis, vol. 65, pp. 41-55 (2002).

International Search Report for PCT/KR2011/006813 (Mar. 26, 2012) (4 pages).

* cited by examiner

US 8,962,901 B2

METHOD OF PRODUCING VALUABLE AROMATICS AND OLEFINS FROM HYDROCARBONACEOUS OILS DERIVED FROM COAL OR WOOD

RELATED APPLICATIONS

This application is a United States national phase application under 35 USC §371 of PCT/KR2011/006813 filed on Sep. 15, 2011, and claims the benefit under 35 USC §119 of Korean patent application number KR 10-2010-0091052 filed Sep. 16, 2010, the disclosures of which are incorporated herein by reference in their entireties.

TECHNICAL FIELD

The present invention relates to a method of producing aromatics and olefins from hydrocarbonaceous oils derived from coal or wood.

BACKGROUND ART

The demand for aromatics, for example, benzene/toluene/xylene, is increasing at a yearly average of 4~6% all over the world, which is a drastic increasing trend that is two times the GDP and three times the demand for general petroleum products. Such an increase is based on the dramatically increasing demand for aromatics in China.

Conventional aromatics (benzene/toluene/xylene) have been produced from pyrolysis gasoline obtained together with fundamental oil products including ethylene, propylene, etc., in naphtha pyrolysis plants using a naphtha feed, or from reformate in catalytic naphtha reformer.

However, because of the drastic increase in the demand for aromatics as noted above, Shortage of naphtha supply are intensifying in the worldwide market including China since 2007, conventional techniques using naphtha cannot meet the increasing aromatic demand because naphtha can be obtained by atmospheric distillation of crude oil only. Hence, there is a need for alternative feed for aromatics, which is usable as a replacement for naphtha, and furthermore, a need to increase the yield of aromatics and olefins is receiving attention.

DISCLOSURE OF INVENTION

Technical Problem

Under such circumstances, the present inventors have ascertained that aromatic components such as benzene, toluene or xylene of which the demand is increasing may be prepared from oils derived from coal or wood and also that it is possible to prepare valuable olefins having high applicability, and therefore the present invention has been devised so as to be adapted for the need of market for the above techniques.

Accordingly, an object of the present invention is to provide a novel method of producing high-concentration aromatics and olefins using oils derived from coal or wood containing a large amount of components having high aromaticity, instead of using a conventional naphtha feed.

Solution to Problem

In order to accomplish the above object, the present invention provides a method of producing aromatics and olefins from oils derived from coal or wood, comprising (a) introducing the oils derived from coal or wood into a hydrogenation and reaction area, so that aromatic components having aromatic rings are partially saturated and cracked; (b) separating components obtained in (a) into hydrocarbonaceous components having 11 or more carbons, hydrocarbonaceous components having 6~10 carbons, and hydrocarbonaceous components having 5 or less carbons; and (c) recirculating the hydrocarbonaceous components having 11 or more carbons separated in (b) back to (a), feeding the hydrocarbonaceous components having 6~10 carbons to an aromatic separation unit and a transalkylation unit so that at least a portion of aromatics is recovered, and feeding the hydrocarbonaceous components having 5 or less carbons to a light separation unit thus obtaining olefins.

Advantageous Effects of Invention

In a method of producing aromatics and olefins according to the present invention, high-concentration aromatics such as benzene, toluene and xylene can be produced using oils including coal tar or light oil resulting from coal carbonation or aromatic compounds resulting from wood pyrolysis, carbonation, destructive distillation, etc., instead of using the conventional naphtha feed, and thus the method according to the present invention can overcome the limitation of throughput of aromatics.

In particular, among a variety of aromatics/olefins, valuable aromatics, for example, benzene and xylene, and valuable olefins such as propylene can be selectively produced, and byproducts which are relatively valueless can be recovered and reprocessed so that their values are increased, thereby greatly increasing the valuableness of final products.

MODE OF THE INVENTION

Hereinafter, a detailed description will be given of the present invention.

The present invention pertains to a method of producing aromatic components including benzene, toluene or xylene and valuable olefins, from oils derived from coal or wood. According to the present invention, oils derived from coal or wood, which are used as a feed, include but are not limited to oils containing aromatic compounds such as coal tar or light oil, wood tar, etc., and any oil containing aromatic components derivable from coal or wood may be used. For example, it is possible to use any materials selected from the group consisting of liquid/solid products obtained by coal liquefaction or coal carbonation, such as coal tar, tar oil, light oil, phenolic oil or carbolic oil, naphthalene oil, wash oil, anthracene oil, light anthracene oil, heavy anthracene oil and pitch, products derived from wood carbonation, such as wood tar, hardwood tar, resinous tar, and combinations thereof.

Figure 1:
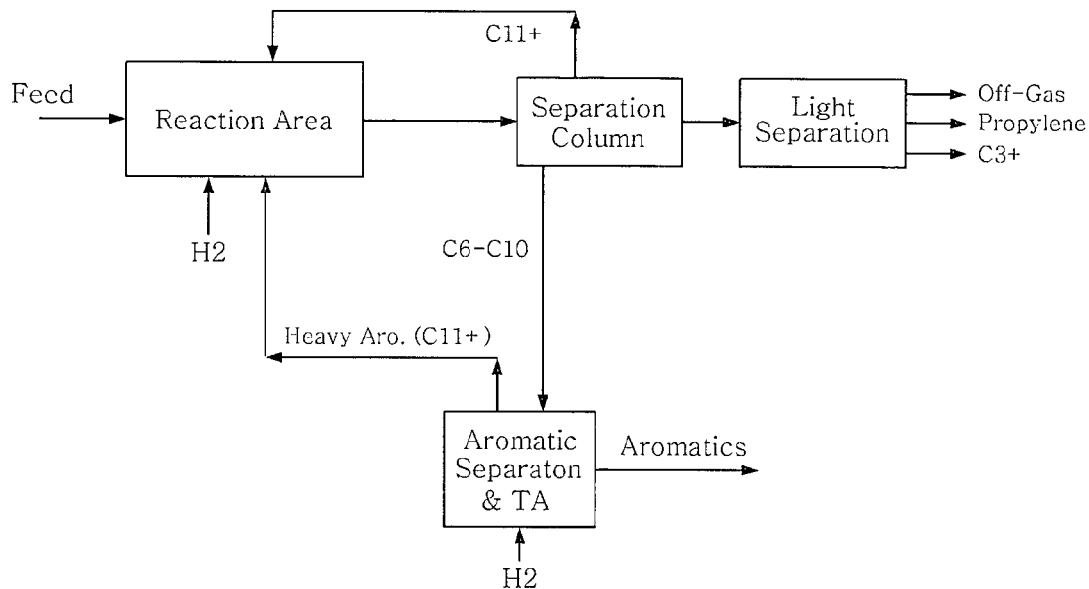
FIG. 1 is a schematic block flow diagram showing a process according to an embodiment of the present invention.
Figure 2:
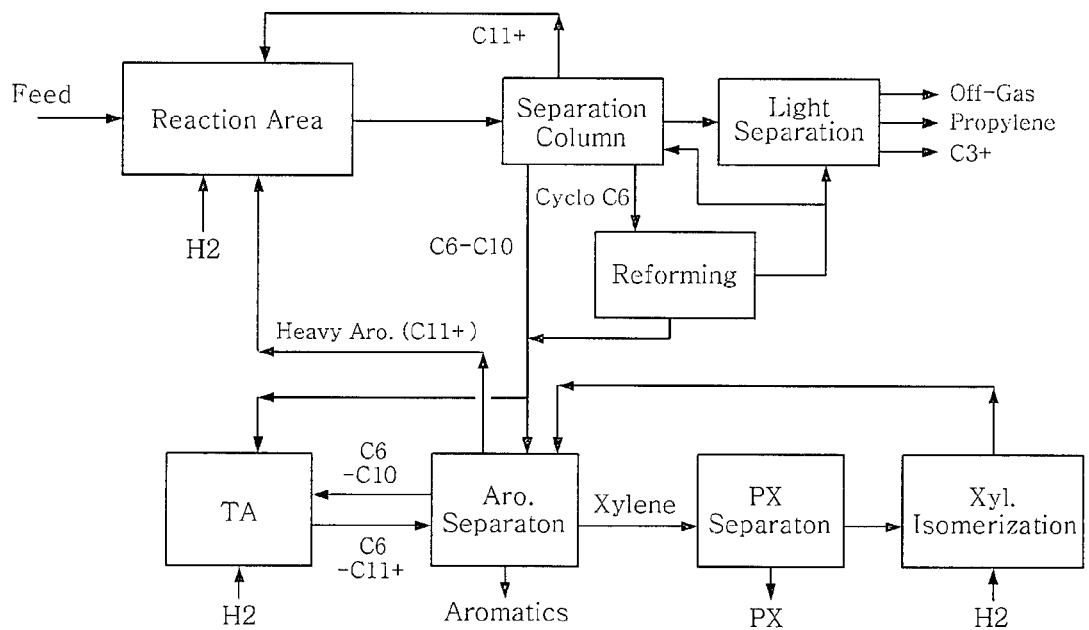
FIG. 2 is a schematic block flow diagram showing a process according to another embodiment of the present invention, including aromatic separation, transalkylation, xylene process and then the recirculation of unconverted oils.

The schematic block flow diagram for the method according to the present invention is shown in FIG. 1. With reference to FIG. 1, the oils derived from coal or wood are introduced into a hydrogenation and reaction area. The oils derived from coal or wood are hydrocarbonaceous compounds consisting 40~99.9% of aromatic components based on the total of hydrocarbonaceous components and having a boiling point of 70~700° C. As the amount of aromatic components of the oils is increased, valuable aromatics may be favorably produced.

According to the present invention, aromatic components having aromatic rings may be partially saturated and cracked in the hydrogenation and reaction area. The hydrogenation and reaction area includes a hydroprocessing unit and a catalytic cracking unit. As such, hydroprocessing and catalytic cracking may be performed in any sequence whatsoever. Specifically, the feed may be introduced into the hydroprocessing unit and then the catalytic cracking unit, or into the catalytic cracking unit and then the hydroprocessing unit.

The hydroprocessing unit of the hydrogenation and reaction area is configured such that hydrogen is supplied from the outside, in which the oils derived from coal and wood are hydrotreated in the presence of a hydrotreating catalyst. By the hydroprocessing reaction, aromatic components having two or more aromatic rings may be partially saturated. Upon such hydroprocessing, an aromatic component having one aromatic ring must not be saturated. This is because the aromatic component having one aromatic ring is a valuable aromatic component or may be converted into a valuable aromatic component by transalkylation which will be described later.

In the hydroprocessing process, the aromatic components having two or more aromatic rings are saturated in such a manner that the aromatic rings other than only one aromatic ring are saturated. This is because it is not easy to perform the cracking of the unnecessary aromatic rings in the downstream catalytic cracking unit.

To obtain the above results, the hydroprocessing unit may operate under conditions including a reaction pressure of 20~100 kg/cm$^2$, a reaction temperature of 150~450° C., and a liquid hourly space velocity (LHSV) of 0.1~4.5 hr$^{-1}$.

Also a catalyst used in the hydroprocessing unit may comprise a carrier composed of one or more selected from the group consisting of alumina, silica, zirconia, titania and activated carbon, and one or more metals selected from the group consisting of Groups 6, 8, 9, and 10 metals. Particularly useful are one or more metals selected from the group consisting of cobalt, molybdenum, nickel and tungsten.

Upon hydroprocessing, not only partial saturation of the aromatic rings but also denitrogenation, desulfurization and deoxygenation that are conducted to remove impurities such as sulfides or nitrogen compounds from the oils may be carried out. Hence, the impurities in the oils may be easily removed without the need to additionally perform removing impurities.

Upon hydroprocessing, the partially saturated feed is fed to the catalytic cracking unit. A catalytic cracking catalyst used in the catalytic cracking unit may include a solid forming catalyst including one or more porous solid acids. The solid acid may include an amorphous solid acid such as silica, alumina or silica-alumina, or a crystalline zeolite molecular sieve having a molar ratio of Si/Al of 300 or less and a pore size of 3~8 Å (Angstrom).

The crystalline zeolite molecular sieve may be a combination of one zeolite molecular sieve selected from among FAU, MOR and BEA which are large zeolite molecular sieves having a pore size of 5.6~7.7 Å so that the aromatic components may react in the pores and one zeolite selected from among MFI, MEL and FER which are medium zeolite molecular sieves having a pore size of 5~6.5 Å. The weight ratio of the large zeolite molecular sieve to the medium zeolite molecular sieve is in the range of 5/95~95/5, and particularly 50/50~95/5.

The catalytic cracking catalyst may be prepared by mixing 10~95 wt % of one or more zeolite molecular sieves selected from the group consisting of FAU, MOR, BEA, MFI, MEL and FER, and 5~90 wt % of an inorganic binder selected from the group consisting of alumina and clay so that they are sprayed and dried to a particle size of 10~300 microns.

Catalytic cracking plays a role in breaking a naphthenic ring or a long branch with two or more carbons attached to a 1-ring aromatic compound. The purpose of hydroprocessing is, in for the aromatic components having two or more aromatic rings, partially saturating the aromatic rings other than the one aromatic ring, so that the naphthenic ring may be broken thus forming valuable aromatic components or raw feed for making aromatic components in the downstream units.

To obtain the above results, the catalytic cracking unit may operate under conditions including a reaction pressure of 10~60 psig, a reaction temperature of 400~600° C., and a ratio of catalyst/oil of 4~10.

The products obtained from the hydrogenation and reaction area are separated into i) hydrocarbonaceous components having 11 or more carbons, ii) hydrocarbonaceous components having 6~10 carbons and iii) hydrocarbonaceous components having 5 or less carbons, by means of a separation column. The hydrocarbonaceous components having 11 or more carbons thus separated are recirculated back to the hydrogenation and reaction area, and the hydrocarbonaceous components having 6~10 carbons are fed to an aromatic separation process and a transalkylation process, and the hydrocarbonaceous components having 5 or less carbons are continuously fed to a light separation unit.

Heavy oils having 11 or more carbons may be converted into valuable aromatic components or valuable olefin components, and are thus recirculated back to the hydrogenation and reaction area. recycled oils recovered by the separation column is about 30% of fresh feed oils, but after recirculation, the amount of oils which should be further recirculated is less than just 3% of the total.

The hydrocarbonaceous components having 5 or less carbons that were separated by the separation column are further separated into off-gas and olefin components by light separation process. The olefin components include 2 or more carbons such as ethylene, propylene, butylene, etc.

The hydrocarbonaceous components having 6~10 carbons that were separated by the separation column are fed to the aromatic separation process and the transalkylation process. As such, among the hydrocarbonaceous components having 6~10 carbons, saturated hydrocarbons including cyclohexane are fed to an additional reformer. A portion of the oils reformated in the reformer is fed to the aromatic separation process and the transalkylation process, and the unconverted oils may be fed to the separation column or the light separation unit. The reformer functions to convert the saturated hydrocarbons into aromatic components at about 400~600° C. using a Pt/Al$_2$O$_3$ or Pt—Re/Al$_2$O$_3$ catalyst in a hydrogen atmosphere. The products obtained by the reformer may include benzene, toluene and xylene, and such unsaturated hydrocarbons are fed to the aromatic separation process and the transalkylation process.

The hydrocarbonaceous components having 6~10 carbons separated by the separation column (and passed through the reformer) are transferred to the aromatic separation process and the transalkylation process. As such, aromatic separation and transalkylation may be performed in any sequence whatsoever. Specifically, (i) the hydrocarbonaceous components having 6~10 carbons may be separated into benzene, toluene, xylene, and hydrocarbonaceous components having 9 or more carbons in the aromatic separation process, after which a portion of the separated oils is transferred to the transalkylation process, thus obtaining a mixture comprising benzene, toluene, xylene, and hydrocarbonaceous components having 9 or more carbons, after which this mixture is further mixed with the remainder of the oils that were not transferred to the transalkylation process, followed by feeding the resulting mixture to the aromatic separation process, thereby recovering the desired aromatics, or (ii) the hydrocarbonaceous components having 6~10 carbons may be directly transferred to the transalkylation unit, thus obtaining a mixture comprising benzene, toluene, xylene, and hydrocarbonaceous components having 9 or more carbons, after which this mixture may be fed to the aromatic separation process, thus recovering the desired aromatics.

Upon transalkylation, dealkylation of alkylaromatic compounds having 9 and more carbons and transalkylation between benzene and aromatic compounds having 9 and more carbons occur simultaneously along with disproportionation of toluene in the presence of a catalyst and transalkylation between toluene and aromatic compounds having 9 and more carbons.

Such dealkylation is an important reaction that produces toluene necessary for disproportionation/transalkylation. Also, transalkylation between benzene and aromatic compounds having 9 and more carbons is regarded as important because it produces toluene and xylene.

On the other hand, olefins including ethylene, propylene, etc., produced by dealkylation, have to be rapidly hydrogenated. In the case where such olefins are not rapidly hydrogenated, they are re-alkylated to aromatic compounds, ultimately lowering the rate of conversion of aromatic compounds having 9 and more carbons. Furthermore, olefin itself may cause polymerization or the like, undesirably facilitating the production of coke that inactivates the catalyst.

The catalyst used for transalkylation is not limited, but may include a catalyst disclosed in U.S. Pat. No. 6,867,340 by the present applicant.

Specifically transalkylation is performed using a catalyst comprising a carrier composed of 10~95 wt % of beta-zeolite or mordenite having a molar ratio of silica/alumina adjusted to 20~200 based on alumina and 5~90 wt % of one or more inorganic binders selected from the group consisting of gamma-alumina, silica, silica alumina, bentonite, kaolin, clinoptilolite and montmorillonite, and a hydrogenation metal composed of, based on 100 parts by weight of the carrier, 0.001~0.5 parts by weight of one or more metals selected from the group consisting of platinum, tin, indium and lead. The other properties of the catalyst are to be found in the above literature. The valuable aromatic components thus produced, namely, benzene and xylene may be recovered and made into products.

After transalkylation, the aromatic components having 11 or more carbons, which are not used as materials to make valuable aromatic components, are recovered, and then may be fed to the hydrogenation reaction area. Also, toluene, xylene and hydrocarbons having 9 or more carbons produced by transalkylation may be fed to a xylene process which will be described later via the aromatic separation process. In the xylene process, separating para-xylene from xylene mixture (composed of ortho-xylene, meta-xylene and para-xylene) and isomerizing the xylene mixture not having para-xylene into para-xylene may be performed.

Also, para-xylene separation for separating only para-xylene from xylene components may be performed using a technique known in the art, such as adsorption, crystallization, etc.

Because para-xylene is much more valuable than ortho-xylene or meta-xylene, the separation and recovery of only para-xylene is favorable.

The xylene mixture including ortho-xylene and meta-xylene, except for para-xylene, may be transferred to the xylene isomerization process. Among the xylene mixture produced by aromatic separation, para-xylene, meta-xylene, and ortho-xylene are in a state of equilibrium. Because only para-xylene is separated by the above separation, the xylene mixture not having para-xylene are equilibrated using a catalyst, whereby para-xylene which is economically valuable may be additionally obtained.

On the other hand, the method according to the present invention may include recovering at least a portion of aromatics, for example, benzene and xylene components, from the transalkylation process and the xylene process, and recirculating the unconverted oils back to the aromatic separation unit. Specifically, a portion of benzene and toluene which are not recovered from the transalkylation process are recirculated back to the aromatic separation process and may thus be further fed to the transalkylation process, and also may be recirculated back to the hydrogenation and reaction area from the aromatic separation process. Upon transalkylation, benzene and toluene may be converted into xylene. Moreover, in the xylene isomerization unit, oils which are not isomerized into para-xylene may be recirculated back to the aromatic separation process, and thus may be fed to the transalkylation process or the xylene process.

Accordingly, all the oils obtained from the xylene isomerization process may be recirculated back to the transalkylation process and the para-xylene separation process via the aromatic cracking process, thus additionally obtaining para-xylene.

Specifically, the recirculation procedure from the transalkylation process and the xylene isomerization process to the aromatic separation process may increase the yield of para-xylene, and improvements in the yield of olefins and valuable aromatics are possible without additional treatment and without wasting materials due to the recirculation from the aromatic separation unit to the hydrogenation and reaction area.

According to an embodiment of the present invention, coal tar is introduced into the hydrogenation and reaction area that performs hydrotreating and hydrocracking. Coal tar cracked in the hydrogenation and reaction area is fed to the separation column so that it is separated into (i) components having 6~10 carbons, (ii) olefin components, and (iii) hydrocarbonaceous components having 11 or more carbons.

After being separated by the separation column, (iii) the oils having 11 or more carbons are mixed with fresh coal tar and then recirculated back to the hydrogenation and reaction area.

By such recirculation, the aromatic components having two or more rings may be cracked to a 1-ring aromatic component by hydroprocessing and catalytic cracking, and hydrocarbonaceous groups having two or more carbons or naphthenic rings may be cracked and converted into valuable aromatic components or materials to make valuable aromatic components.

When the recirculation is performed in this way, the amount of aromatic components having two or more rings may be drastically reduced, compared to when the recirculation is not performed. Furthermore, the amount thereof which is converted into valuable aromatics or materials to make valuable aromatics may be considerably increased. For example, in the case where recirculation is performed, benzene which is the valuable aromatic component is increased by 15~25%, and xylene may be increased by 160~197%.

Also, (i) the components having 6~10 carbons are fed to the aromatic separation unit, thus obtaining benzene, toluene, xylene and hydrocarbonaceous components having 9 or more carbons, which are then fed to the transalkylation process, after which the components including benzene, toluene and xylene produced by the transalkylation process are recirculated back to the aromatic separation unit, the transalkylation unit, the xylene treatment unit and the hydrogenation reaction area, via the aromatic separation unit, whereby the total yield of benzene and para-xylene is increased by about 75~85%.

Thus, when the above recirculation step is added, accumulation of unnecessary components upon transalkylation and xylene treatment is prevented, and the components which are not used as materials to make valuable aromatic components may be converted into valuable aromatic components, thus increasing the yield of valuable aromatics. The recirculation effects are described in detail in the following example.

In order to additionally explain the principle of the present invention, the example is described below, but the present example is not supposed to limit the scope of the present invention as envisioned by the present inventors.

Example

Production of Valuable Aromatics and Olefins from Coal Tar using Hydrogenation Reaction, Aromatic Separation, and Transalkylation The properties and compositions of the oils derived from coal used in this Example may differ depending on the kind of feed and operating conditions. In the present example, as oils derived from coal, coal tar having a boiling point of 78~350° C. and having the composition shown in Table 1 below was prepared.

TABLE 1

| Components | Feed Amount |
|---|---|
| Flow rate | 100.00 |
| Coke | 0.00 |
| $H_2S$ | 0.00 |
| $H_2$ | 0.00 |
| Paraffin + Olefin | 0.77 |
| Ethylene | 0.00 |
| Propylene | 0.00 |
| Butylene | 0.00 |
| Naphthene | 0.00 |
| Total of Aromatics | 99.23 |
| Total of 1-ring Aromatics | 9.73 |
| 1-ring Aromatic without naphthenic ring | 6.30 |
| BTX + C9, C10 | 6.30 |
| BTX | 4.35 |
| B + X | 3.64 |
| T + C9 + C10 | 2.65 |
| B | 2.05 |
| T | 0.70 |
| X | 1.59 |
| C9 | 1.65 |
| C10 | 0.30 |
| 1-ring Aromatic with one naphthenic ring | 3.43 |
| 1-ring Aromatic with two naphthenic rings | 0.00 |
| Total of 2-ring Aromatics | 89.50 |
| 2-ring Aromatic without naphthenic ring | 66.92 |
| 2-ring Aromatic with one naphthenic ring | 22.58 |
| 2-ring Aromatic with two naphthenic rings | 0.00 |
| Total of 3-ring Aromatics | 0.00 |
| Others | 0.00 |

The coal tar having the above composition was fed to a hydroprocessing process. Hydrotreating was performed in a fixed-bed reactor in the presence of a catalyst comprising an alumina/silica carrier and nickel/molybdenum metals. The hydrotreating reaction conditions are shown in Table 2 below.

TABLE 2

| Catalyst | $NiMo/Al_2O_3$ |
|---|---|
| Operating Conditions | |
| Reaction Pressure, kg/cm$^2$ | 60 |
| LHSV, hr$^{-1}$ | 1.5 |
| Reaction Temperature, ° C. | 300 |

After hydroprocessing, the composition was changed as shown in Table 3 below.

TABLE 3

| Components | Feed Amount | After Hydrotreating |
|---|---|---|
| Flow rate | 100.00 | 102.09 |
| Coke | 0.00 | 0.00 |
| $H_2S$ | 0.00 | 0.00 |
| $H_2$ | 0.00 | 0.00 |
| Paraffin + Olefin | 0.77 | 0.79 |
| Ethylene | 0.00 | 0.00 |
| Propylene | 0.00 | 0.00 |
| Butylene | 0.00 | 0.00 |
| Naphthene | 0.00 | 0.00 |
| Total of Aromatics | 99.23 | 101.30 |
| Total of 1-ring Aromatics | 9.73 | 81.19 |
| 1-ring Aromatic without naphthenic ring | 6.30 | 6.43 |
| BTX + C9, C10 | 6.30 | 6.43 |
| BTX | 4.35 | 4.44 |
| B + X | 3.64 | 3.72 |
| T + C9 + C10 | 2.65 | 2.71 |
| B | 2.05 | 2.09 |
| T | 0.70 | 0.72 |
| X | 1.59 | 1.63 |
| C9 | 1.65 | 1.68 |
| C10 | 0.30 | 0.31 |
| 1-ring Aromatic with one naphthenic ring | 3.43 | 59.73 |
| 1-ring Aromatic with two naphthenic rings | 0.00 | 15.04 |
| Total of 2-ring Aromatics | 89.50 | 20.11 |
| 2-ring Aromatic without naphthenic ring | 66.92 | 12.10 |
| 2-ring Aromatic with one naphthenic ring | 22.58 | 8.01 |
| 2-ring Aromatic with two naphthenic rings | 0.00 | 0.00 |
| Total of 3-ring Aromatics | 0.00 | 0.00 |
| Others | 0.00 | 0.00 |

As is apparent from Table 3, before hydroprocessing, the amount of the aromatic components having two or more aromatic rings was considerable but was drastically reduced after hydroprocessing. Also the amount of the 1-ring aromatic component was increased about 8 times or more, and in particular, the amount of the 1-ring aromatic component having the naphthenic ring was increased from about 3.4 to about 74.7, namely at least 21 times, based on a value of 100 for the feed. The 1-ring aromatic component having the naphthenic ring may be formed into a valuable aromatic component or a direct material to make the valuable aromatic component by breaking the naphthenic ring in the downstream catalytic cracking process.

The products obtained from the hydroprocessing process were supplied to a fluidized-bed catalytic cracking reactor that enables the continuous regeneration of a catalyst, so that catalytic cracking was carried out. The catalyst used herein was an easily commercially available FAU zeolite-containing silica/alumina catalyst (alumina 49%, silica 33%, rare-earth metal 2% and the other inorganic binder). Also, the catalytic cracking operating conditions were a reaction temperature of 549° C., a reaction pressure of 25.3 psig and a catalyst/oil ratio of 8.

After catalytic cracking, the composition was changed as shown in Table 4 below.

TABLE 4

| Components | Feed Amount | After Hydrotreating | After Catalytic Cracking |
|---|---|---|---|
| Flow rate | 100.00 | 102.09 | 102.09 |
| Coke | 0.00 | 0.00 | 0.08 |
| $H_2S$ | 0.00 | 0.00 | 0.00 |
| $H_2$ | 0.00 | 0.00 | 0.00 |
| Paraffin + Olefin | 0.77 | 0.79 | 13.55 |
| Ethylene | 0.00 | 0.00 | 0.43 |
| Propylene | 0.00 | 0.00 | 0.92 |
| Butylene | 0.00 | 0.00 | 1.58 |
| Naphthene | 0.00 | 0.00 | 0.20 |
| Total of Aromatics | 99.23 | 101.30 | 85.97 |
| Total of 1-ring Aromatics | 9.73 | 81.19 | 37.62 |
| 1-ring Aromatic without naphthenic ring | 6.30 | 6.43 | 27.51 |
| BTX + C9, C10 | 6.30 | 6.43 | 27.43 |
| BTX | 4.35 | 4.44 | 21.27 |
| B + X | 3.64 | 3.72 | 13.50 |
| T + C9 + C10 | 2.65 | 2.71 | 13.93 |
| B | 2.05 | 2.09 | 6.84 |
| T | 0.70 | 0.72 | 7.77 |
| X | 1.59 | 1.63 | 6.66 |
| C9 | 1.65 | 1.68 | 4.33 |
| C10 | 0.30 | 0.31 | 1.84 |
| 1-ring Aromatic with one naphthenic ring | 3.43 | 59.73 | 10.11 |
| 1-ring Aromatic with two naphthenic rings | 0.00 | 15.04 | 0.00 |
| Total of 2-ring Aromatics | 89.50 | 20.11 | 47.90 |
| 2-ring Aromatic without naphthenic ring | 66.92 | 12.10 | 39.63 |
| 2-ring Aromatic with one naphthenic ring | 22.58 | 8.01 | 8.27 |
| 2-ring Aromatic with two naphthenic rings | 0.00 | 0.00 | 0.00 |
| Total of 3-ring Aromatics | 0.00 | 0.00 | 0.44 |
| Others | 0.00 | 0.00 | 2.29 |

As is apparent from Table 4, compared to the feed before catalytic cracking, namely, the feed after hydroprocessing, the amount of benzene and xylene which are valuable aromatic components was increased by 262%. Also, the amount of toluene/C9/C10 which are the materials to make the benzene/xylene by subsequent transalkylation was increased by about 410%.

The products obtained by catalytic cracking included light olefins comprising 0.43 wt % of ethylene, 0.92 wt % of propylene and 1.58 wt % of butylene, which were absent from the original composition.

Among the components produced by catalytic cracking, the light olefins were recovered, and only components having 6~10 carbons were fed to the transalkylation process. The catalyst used in the transalkylation process was composed of a carrier comprising 50 wt % of mordenite having a molar ratio of silica/alumina of 90 and 50 wt % of gamma-alumina binder and 0.05 parts by weight of platinum and 0.5 parts by weight of tin supported thereon. The composition of the products obtained by transalkylation is shown in Table 5 below.

TABLE 5

| Components | Feed Amount | After Hydrotreating | After Catalytic Cracking | After Transalkylation |
|---|---|---|---|---|
| Flow rate | 100.00 | 102.09 | 102.09 | 102.54 |
| Coke | 0.00 | 0.00 | 0.08 | 0.08 |
| $H_2S$ | 0.00 | 0.00 | 0.00 | 0.00 |
| $H_2$ | 0.00 | 0.00 | 0.00 | 0.00 |
| Paraffin + Olefin | 0.77 | 0.79 | 13.55 | 19.04 |
| Ethylene | 0.00 | 0.00 | 0.43 | 0.43 |
| Propylene | 0.00 | 0.00 | 0.92 | 0.92 |
| Butylene | 0.00 | 0.00 | 1.58 | 1.58 |
| Naphthene | 0.00 | 0.00 | 0.20 | 0.04 |
| Total of Aromatics | 99.23 | 101.30 | 85.97 | 81.10 |
| Total of 1-ring Aromatics | 9.73 | 81.19 | 37.62 | 32.75 |
| 1-ring Aromatic without naphthenic ring | 6.30 | 6.43 | 27.51 | 26.30 |
| BTX + C9, C10 | 6.30 | 6.43 | 27.43 | 25.53 |
| BTX | 4.35 | 4.44 | 21.27 | 25.44 |
| B + X | 3.64 | 3.72 | 13.50 | 25.44 |
| T + C9 + C10 | 2.65 | 2.71 | 13.93 | 0.09 |
| B | 2.05 | 2.09 | 6.84 | 16.05 |
| T | 0.70 | 0.72 | 7.77 | 0.00 |
| X | 1.59 | 1.63 | 6.66 | 9.39 |
| C9 | 1.65 | 1.68 | 4.33 | 0.00 |
| C10 | 0.30 | 0.31 | 1.84 | 0.09 |
| 1-ring Aromatic with one naphthenic ring | 3.43 | 59.73 | 10.11 | 6.45 |
| 1-ring Aromatic with two naphthenic rings | 0.00 | 15.04 | 0.00 | 0.00 |
| Total of 2-ring Aromatics | 89.50 | 20.11 | 47.90 | 47.90 |
| 2-ring Aromatic without naphthenic ring | 66.92 | 12.10 | 39.63 | 39.63 |
| 2-ring Aromatic with one naphthenic ring | 22.58 | 8.01 | 8.27 | 8.27 |
| 2-ring Aromatic with two naphthenic rings | 0.00 | 0.00 | 0.00 | 0.00 |
| Total of 3-ring Aromatics | 0.00 | 0.00 | 0.44 | 0.44 |
| Others | 0.00 | 0.00 | 2.29 | 2.29 |

As is apparent from Table 5, compared to the feed before transalkylation, the feed after transalkylation had benezene as the valuable aromatic component, the amount of which was increased by 134%, and xylene which further increased in amount by 41%. Also, the total of benzene and xylene was increased by about 88%. Because the transalkylation was not a cracking procedure, there was no additional increase in the amount of olefins.

Production of Valuable Aromatics and Olefins from Coal Tar by Recirculation of Hydrocarbons having 11 or more Carbons In the process of producing valuable aromatics and olefins, the same feed and reaction conditions were applied, with the exception that the hydrocarbonaceous components having 11 or more carbons resulting from hydroprocessing and catalytic cracking were recirculated back to the hydrogenation and reaction area.

C tar feed (A0), the product (A1) obtained without recirculating hydrocarbons having 11 or more carbons, and the product (A2) obtained by recirculating hydrocarbons having 11 or more carbons are shown in Table 6 below.

TABLE 6

| Components | A0 | A1 | A2 |
|---|---|---|---|
| Flow rate | 100.00 | 102.54 | 105.55 |
| Coke | 0.00 | 0.08 | 6.88 |
| $H_2S$ | 0.00 | 0.00 | 0.00 |
| $H_2$ | 0.00 | 0.00 | 0.13 |
| Paraffin + Olefin | 0.77 | 19.04 | 50.92 |
| Ethylene | 0.00 | 0.43 | 2.21 |
| Propylene | 0.00 | 0.92 | 8.02 |
| Butylene | 0.00 | 1.58 | 4.31 |
| Naphthene | 0.00 | 0.04 | 0.08 |
| Total of Aromatics | 99.23 | 81.10 | 47.54 |
| Total of 1-ring Aromatics | 9.73 | 32.75 | 47.54 |
| 1-ring Aromatic without naphthenic ring | 6.30 | 26.30 | 47.54 |
| BTX + C9, C10 | 6.30 | 25.53 | 46.30 |
| BTX | 4.35 | 25.44 | 46.30 |
| B + X | 3.64 | 25.44 | 46.30 |
| T + C9 + C10 | 2.65 | 0.09 | 0.00 |
| B | 2.05 | 16.05 | 19.30 |
| T | 0.70 | 0.00 | 0.00 |
| X | 1.59 | 9.39 | 27.00 |
| C9 | 1.65 | 0.00 | 0.00 |
| C10 | 0.30 | 0.09 | 0.00 |
| 1-ring Aromatic with one naphthenic ring | 3.43 | 6.45 | 0.00 |
| 1-ring Aromatic with two naphthenic rings | 0.00 | 0.00 | 0.00 |
| Total of 2-ring Aromatics | 89.50 | 47.90 | 0.00 |
| 2-ring Aromatic without naphthenic ring | 66.92 | 39.63 | 0.00 |
| 2-ring Aromatic with one naphthenic ring | 22.58 | 8.27 | 0.00 |
| 2-ring Aromatic with two naphthenic rings | 0.00 | 0.00 | 0.00 |
| Total of 3-ring Aromatics | 0.00 | 0.44 | 0.00 |
| Others | 0.00 | 2.29 | 0.00 |

As is apparent from Table 6, recirculation was additionally performed, whereby the aromatic components having two or more rings were excluded and as the valuable aromatic components, benzene was increased by 21% and xylene was further increased by 187%. The total of benzene and xylene was increased by about 82%. Also, the total of light olefins, including ethylene, propylene and butylene was increased about 5 times. Therefore, the valuable aromatics and olefins could be obtained at higher yields because of recirculation.

Production of Valuable Aromatics and Olefins from Coal Tar by Recirculation of Unconverted Oils after Transalkylation In the process of producing valuable aromatics and olefins by recirculating the hydrocarbonaceous components having 11 or more carbons to the hydroprocessing process, the same feed and reaction conditions were applied, with the exception that a portion of benzene, toluene, xylene and components having 9 or more carbons resulting from transalkylation was repetitively recirculated back to the transalkylation process and the hydrogenation and reaction area via the aromatic separation unit.

Coal tar feed (A0), the product (A1) obtained without recirculating hydrocarbons having 11 or more carbons, the product (A2) obtained by recirculating hydrocarbons having 11 or more carbons, and the product (A3) obtained by recirculating unconverted heavy oils after transalkylation are shown in Table 7 below.

TABLE 7

| Components | A0 | A1 | A2 | A3 |
|---|---|---|---|---|
| Flow rate | 100.00 | 102.54 | 105.55 | 105.76 |
| Coke | 0.00 | 0.08 | 6.88 | 6.88 |
| $H_2S$ | 0.00 | 0.00 | 0.00 | 0.00 |
| $H_2$ | 0.00 | 0.00 | 0.13 | 0.13 |
| Paraffin + Olefin | 0.77 | 19.04 | 50.92 | 51.11 |
| Ethylene | 0.00 | 0.43 | 2.21 | 2.35 |
| Propylene | 0.00 | 0.92 | 8.02 | 8.20 |
| Butylene | 0.00 | 1.58 | 4.31 | 4.44 |
| Naphthene | 0.00 | 0.04 | 0.08 | 0.09 |
| Total of Aromatics | 99.23 | 81.10 | 47.54 | 47.56 |
| Total of 1-ring Aromatics | 9.73 | 32.75 | 47.54 | 47.56 |
| 1-ring Aromatic without naphthenic ring | 6.30 | 26.30 | 47.54 | 47.56 |
| BTX + C9, C10 | 6.30 | 25.53 | 46.30 | 47.56 |
| BTX | 4.35 | 25.44 | 46.30 | 47.56 |
| B + X | 3.64 | 25.44 | 46.30 | 47.56 |
| T + C9 + C10 | 2.65 | 0.09 | 0.00 | 0.00 |
| B | 2.05 | 16.05 | 19.30 | 19.26 |
| T | 0.70 | 0.00 | 0.00 | 0.00 |
| X | 1.59 | 9.39 | 27.00 | 28.30 |
| C9 | 1.65 | 0.00 | 0.00 | 0.00 |
| C10 | 0.30 | 0.09 | 0.00 | 0.00 |
| 1-ring Aromatic with one naphthenic ring | 3.43 | 6.45 | 0.00 | 0.00 |
| 1-ring Aromatic with two naphthenic rings | 0.00 | 0.00 | 0.00 | 0.00 |
| Total of 2-ring Aromatics | 89.50 | 47.90 | 0.00 | 0.00 |
| 2-ring Aromatic without naphthenic ring | 66.92 | 39.63 | 0.00 | 0.00 |
| 2-ring Aromatic with one naphthenic ring | 22.58 | 8.27 | 0.00 | 0.00 |
| 2-ring Aromatic with two naphthenic rings | 0.00 | 0.00 | 0.00 | 0.00 |
| Total of 3-ring Aromatics | 0.00 | 0.44 | 0.00 | 0.00 |
| Others | 0.00 | 2.29 | 0.00 | 0.00 |

As is apparent from Table 7, recirculation was carried out two times, whereby the amount of benzene and xylene which are valuable aromatic components was increased by 1.2 wt %, and the amount of light olefins such as ethylene, propylene and butylene was increased by 0.46 wt %, compared to when recirculation was performed one time. Therefore, the valuable aromatics and olefins could be obtained at higher yields by carrying out recirculation two times.

Production of Valuable Aromatics and Olefins from Coal Tar by Xylene process after Transalkylation In the recirculation of unconverted oils after transalkylation, the same feed and reaction conditions were applied, with the exception that the xylene components obtained by transalkylation were treated with xylene process comprising para-xylene separation and para-xylene isomerization.

Coal tar feed (A0), the product (A1) obtained without recirculating hydrocarbons having 11 or more carbons, the product (A2) obtained by recirculating hydrocarbons having 11 or more carbons, the product (A3) obtained by recirculating unconverted heavy oils after transalkylation, and the product (A4) obtained by xylene isomerization and separation are shown in Table 8 below.

TABLE 8

| Components | A0 | A1 | A2 | A3 | A4 |
|---|---|---|---|---|---|
| Flow rate | 100.00 | 102.54 | 105.55 | 105.76 | 105.77 |
| Coke | 0.00 | 0.08 | 6.88 | 6.88 | 6.88 |
| $H_2S$ | 0.00 | 0.00 | 0.00 | 0.00 | 0.00 |
| $H_2$ | 0.00 | 0.00 | 0.13 | 0.13 | 0.13 |
| Paraffin + Olefin | 0.77 | 19.04 | 50.92 | 51.11 | 51.54 |
| Ethylene | 0.00 | 0.43 | 2.21 | 2.35 | 2.35 |
| Propylene | 0.00 | 0.92 | 8.02 | 8.20 | 8.20 |
| Butylene | 0.00 | 1.58 | 4.31 | 4.44 | 4.44 |
| Naphthene | 0.00 | 0.04 | 0.08 | 0.09 | 0.09 |
| Total of Aromatics | 99.23 | 81.10 | 47.54 | 47.56 | 47.13 |
| Total of 1-ring Aromatics | 9.73 | 32.75 | 47.54 | 47.56 | 47.13 |

TABLE 8-continued

| Components | A0 | A1 | A2 | A3 | A4 |
|---|---|---|---|---|---|
| 1-ring Aromatic without naphthenic ring | 6.30 | 26.30 | 47.54 | 47.56 | 47.13 |
| BTX + C9, C10 | 6.30 | 25.53 | 47.16 | 47.56 | 47.13 |
| BTX | 4.35 | 25.44 | 47.16 | 47.56 | 47.13 |
| B + X | 3.64 | 25.44 | 47.16 | 47.56 | 47.13 |
| T + C9 + C10 | 2.65 | 0.09 | 0.00 | 0.00 | 0.00 |
| B | 2.05 | 16.05 | 19.30 | 19.26 | 19.95 |
| T | 0.70 | 0.00 | 0.00 | 0.00 | 0.00 |
| Mixed-X | 0.97 | 8.83 | 27.00 | 27.37 | 27.18 |
| EB | 0.63 | 0.56 | 0.86 | 0.92 | 0.00 |
| C9 | 1.65 | 0.00 | 0.00 | 0.00 | 0.00 |
| C10 | 0.30 | 0.09 | 0.00 | 0.00 | 0.00 |
| 1-ring Aromatic with one naphthenic ring | 3.43 | 6.45 | 0.00 | 0.00 | 0.00 |
| 1-ring Aromatic with two naphthenic rings | 0.00 | 0.00 | 0.00 | 0.00 | 0.00 |
| Total of 2-ring Aromatics | 89.50 | 47.90 | 0.00 | 0.00 | 0.00 |
| 2-ring Aromatic without naphthenic ring | 66.92 | 39.63 | 0.00 | 0.00 | 0.00 |
| 2-ring Aromatic with one naphthenic ring | 22.58 | 8.27 | 0.00 | 0.00 | 0.00 |
| 2-ring Aromatic with two naphthenic rings | 0.00 | 0.00 | 0.00 | 0.00 | 0.00 |
| Total of 3-ring Aromatics | 0.00 | 0.44 | 0.00 | 0.00 | 0.00 |
| Others | 0.00 | 2.29 | 0.00 | 0.00 | 0.00 |

As is apparent from Table 8, almost of the xylene mixture could be converted into para-xylene which is a valuable product by para-xylene separation and para-xylene isomerization, and ethylbenzene (EB) which is an impurity in the xylene component was completely removed and converted into benzene. Therefore, the yield of valuable aromatics could be increased by additionally carrying out xylene treatment.

Although the embodiments of the present invention have been disclosed for illustrative purposes, those skilled in the art will appreciate that a variety of different modifications, additions and substitutions are possible, without departing from the scope and spirit of the invention as disclosed in the accompanying claims. Accordingly, such modifications, additions and substitutions should also be understood as falling within the scope of the present invention.

The invention claimed is:

1. A method for producing aromatics and olefins from hydrocarbonaceous oils derived from coal or wood comprising:
   a) introducing oils derived from coal or wood comprising aromatic compounds into a hydrogenation and reaction area comprising a hydroprocessing process and a catalytic cracking process;
   b) hydroprocessing the oils in the presence of a hydroprocessing catalyst to partially saturate aromatic components having two or more aromatic rings into aromatic components having one aromatic ring, such that an amount of aromatic components having one aromatic ring in the oils is increased;
   c) catalytically cracking the hydroprocessed oils in the presence of a cracking catalyst to form catalytically cracked oils;
   d) separating the catalytically cracked oils into
      i) hydrocarbonaceous components having 11 or more carbons,
      ii) hydrocarbonaceous components having 6-10 carbons, and
      iii) hydrocarbonaceous components having 5 or less carbons;
   e) recirculating the hydrocarbonaceous components having 11 or more carbons to the hydrogenation and reaction area;
   f) feeding the hydrocarbonaceous components having 6-10 carbons to an aromatic separation process or a transalkylation process,
      wherein:
         hydrocarbonaceous components having 6-10 carbons fed to the aromatic separation process are separated into a first portion and a second portion,
         the first portion is fed to a transalkylation process and contacted with a transalkylation catalyst to form a transalkylated product comprising benzene, toluene, xylenes and hydrocarbonaceous components having 9 or more carbons,
         the transalkylated product is mixed with the second portion in the aromatic separation process, and
         hydrocarbonaceous components having 11 or more carbons, hydrocarbonaceous components having 6-10 carbons, a xylene mixture comprising ortho-xylene, meta-xylene, and para-xylene, and/or an aromatics stream comprising benzene, toluene, xylenes or mixtures thereof, are separated in the aromatic separation process; or
         hydrocarbonaceous components having 6-10 carbons fed to the transalkylation process are contacted with a transalkylation catalyst to form a transalkylated product comprising benzene, toluene, xylenes and hydrocarbonaceous components having 9 or more carbons,
         the transalkylated product is fed to an aromatic separation process, and
         hydrocarbonaceous components having 11 or more carbons, hydrocarbonaceous components having 6-10 carbons, a xylene mixture comprising ortho-xylene, meta-xylene, and para-xylene, and/or an aromatics stream comprising benzene, toluene, xylenes or mixtures thereof, are separated in the aromatic separation process; and
   g) feeding the hydrocarbonaceous components having 5 or less carbons to a light oil separation process to recover olefins;
      wherein the oils derived from coal or wood contain 40-99.9 wt % aromatic components based on total hydrocarbonaceous components, have a boiling point of 70-700° C., and comprise coal tar, tar oil, light oil, phenolic oil or carbolic oil, naphthalene oil, wash oil, anthracene oil, light anthracene oil, heavy anthracene oil, pitch, wood tar, hardwood tar, resinous tar or mixtures thereof.

2. The method of claim 1, further comprising (h) feeding the xylene mixture separated in the aromatic separation process to a xylene treatment process, separating para-xylene from the xylene mixture, isomerizing meta- and ortho-xylenes into para-xylene, and recirculating isomerized product other than para-xylene to the aromatic separation process.

3. The method of claim 1, wherein the hydroprocessing catalyst comprises a carrier composed of one or more selected from the group consisting of alumina, silica, zirconia, titania, and activated carbon, and one or more metals selected from the group consisting of Groups 6, 8, 9 and 10 metals.

4. The method of claim 1, wherein the cracking catalyst comprises a zeolite selected from the group consisting of FAU, MOR, BEA, MFI, MEL and FER, or combinations thereof, and an inorganic binder selected from the group consisting of alumina and clay.

5. The method of claim 1, further comprising recirculating the hydrocarbonaceous components having 11 or more carbons obtained from the aromatic separation process to the hydrogenation and reaction area and feeding the hydrocarbonaceous components having 6-10 carbons separated in the aromatic separation process to the transalkylation process.

6. The method of claim 1, further comprising (d') separating saturated hydrocarbons including cyclohexane from the (ii) hydrocarbonaceous components having 6-10 carbons prior to step (f), feeding the saturated hydrocarbonaceous components to a reformer to form unsaturated hydrocarbon components, and feeding the unsaturated hydrocarbon components to step (f).

7. The method of claim 6, wherein the reformer is operated at a temperature of 400-600° C. in a hydrogen atmosphere using Pt/Al$_2$O$_3$ or Pt—Re/Al$_2$O$_3$ catalyst.

8. The method of claim 1, wherein the transalkylation catalyst comprises:
  a carrier composed of 10-95 wt % of beta-zeolite or mordenite having a molar ratio of silica/alumina adjusted to 20-200 based on alumina and 5-90 wt % of one or more inorganic binders selected from the group consisting of gamma-alumina, silica, silica alumina, bentonite, kaolin, clinoptilolite and montmorillonite; and
  a hydrogenation metal composed of, based on 100 parts by weight of the carrier, 0.001-0.5 parts by weight of one or more metals selected from the group consisting of platinum, tin, indium and lead.

9. A method for producing aromatics and olefins from hydrocarbonaceous oils derived from coal or wood comprising:
  a) introducing oils derived from coal or wood comprising aromatic compounds into a hydrogenation and reaction area comprising a catalytic cracking process and a hydroprocessing process;
  b) catalytically cracking the oils in the presence of a cracking catalyst to form catalytically cracked oils;
  c) hydroprocessing the catalytically cracked oils in the presence of a hydroprocessing catalyst to partially saturate aromatic components having two or more aromatic rings into aromatic components having one aromatic ring, such that an amount of aromatic components having one aromatic ring in the catalytically cracked oils is increased, to form hydroprocessed oils;
  d) separating the hydroprocessed oils into
    i) hydrocarbonaceous components having 11 or more carbons,
    ii) hydrocarbonaceous components having 6-10 carbons, and
    iii) hydrocarbonaceous components having 5 or less carbons;
  e) recirculating the hydrocarbonaceous components having 11 or more carbons to the hydrogenation and reaction area;
  f) feeding the hydrocarbonaceous components having 6-10 carbons to an aromatic separation process or a transalkylation process,
    wherein:
      hydrocarbonaceous components having 6-10 carbons fed to the aromatic separation process are separated into a first portion and a second portion,
      the first portion is fed to a transalkylation process and contacted with a transalkylation catalyst to form a transalkylated product comprising benzene, toluene, xylenes and hydrocarbonaceous components having 9 or more carbons,
      the transalkylated product is mixed with the second portion in the aromatic separation process, and hydrocarbonaceous components having 11 or more carbons, hydrocarbonaceous components having 6-10 carbons, a xylene mixture comprising ortho-xylene, meta-xylene, and para-xylene, and/or an aromatics stream comprising benzene, toluene, xylenes or mixtures thereof, are separated in the aromatic separation process; or
      hydrocarbonaceous components having 6-10 carbons fed to the transalkylation process are contacted with a transalkylation catalyst to form a transalkylated product comprising benzene, toluene, xylenes and hydrocarbonaceous components having 9 or more carbons,
      the transalkylated product is fed to an aromatic separation process, and
      hydrocarbonaceous components having 11 or more carbons, hydrocarbonaceous components having 6-10 carbons, a xylene mixture comprising ortho-xylene, meta-xylene, and para-xylene, and/or an aromatics stream comprising benzene, toluene, xylenes or mixtures thereof, are separated in the aromatic separation process; and
  g) feeding the hydrocarbonaceous components having 5 or less carbons to a light oil separation process to recover olefins;
    wherein the oils derived from coal or wood contain 40-99.9 wt % aromatic components based on total hydrocarbonaceous components, have a boiling point of 70-700° C., and comprise coal tar, tar oil, light oil, phenolic oil or carbolic oil, naphthalene oil, wash oil, anthracene oil, light anthracene oil, heavy anthracene oil, pitch, wood tar, hardwood tar, resinous tar or mixtures thereof.

10. The method of claim 9, further comprising (h) feeding the xylene mixture separated in the aromatic separation process to a xylene treatment process, separating para-xylene from the xylene mixture, isomerizing meta- and ortho-xylenes into para-xylene, and recirculating isomerized product other than para-xylene to the aromatic separation process.

11. The method of claim 9, wherein the hydroprocessing catalyst comprises a carrier composed of one or more selected from the group consisting of alumina, silica, zirconia, titania, and activated carbon, and one or more metals selected from the group consisting of Groups 6, 8, 9 and 10 metals.

12. The method of claim 9, wherein the cracking catalyst comprises a zeolite selected from the group consisting of FAU, MOR, BEA, MFI, MEL and FER, or combinations thereof, and an inorganic binder selected from the group consisting of alumina and clay.

13. The method of claim 9, further comprising recirculating the hydrocarbonaceous components having 11 or more carbons obtained from the aromatic separation process to the hydrogenation and reaction area and feeding the hydrocarbonaceous components having 6-10 carbons separated in the aromatic separation process to the transalkylation process.

14. The method of claim 9, further comprising (d') separating saturated hydrocarbons including cyclohexane from the (ii) hydrocarbonaceous components having 6-10 carbons prior to step (f), feeding the saturated hydrocarbonaceous components to a reformer to form unsaturated hydrocarbon components, and feeding the unsaturated hydrocarbon components to step (f).

15. The method of claim 14, wherein the reformer is operated at a temperature of 400-600° C. in a hydrogen atmosphere using Pt/Al$_2$O$_3$ or Pt—Re/Al$_2$O$_3$ catalyst.

16. The method of claim 9, wherein the transalkylation catalyst comprises:
  a carrier composed of 10-95 wt % of beta-zeolite or -mordenite having a molar ratio of silica/alumina adjusted to 20-200 based on alumina and 5-90 wt % of one or more inorganic binders selected from the group consisting of gamma-alumina, silica, silica alumina, bentonite, kaolin, clinoptilolite and montmorillonite; and a hydrogenation metal composed of, based on 100 parts by weight of the carrier, 0.001-0.5 parts by weight of one or more metals selected from the group consisting of platinum, tin, indium and lead.

* * * * *